United States Patent
McIntyre et al.

(10) Patent No.: US 9,242,111 B2
(45) Date of Patent: Jan. 26, 2016

(54) TESTING OF DEFIBRILLATOR ELECTRODES

(75) Inventors: Allister Robert McIntyre, Newtownards Co Down (GB); Johnny Houston Anderson, Holywood Co Down (GB)

(73) Assignee: Heartsine Technologies Limited, Belfast (GB)

( * ) Notice: Subject to any disclaimer, the term of this patent is extended or adjusted under 35 U.S.C. 154(b) by 217 days.

(21) Appl. No.: 13/616,271

(22) Filed: Sep. 14, 2012

(65) Prior Publication Data

US 2013/0069679 A1  Mar. 21, 2013

(30) Foreign Application Priority Data

Sep. 15, 2011 (GB) .................................. 1115954.8

(51) Int. Cl.
 *A61N 1/39* (2006.01)
 *A61N 1/372* (2006.01)
 A61N 1/08 (2006.01)

(52) U.S. Cl.
 CPC .......... *A61N 1/3931* (2013.01); *A61N 1/37241* (2013.01); *A61N 2001/083* (2013.01); *A61N 2001/37294* (2013.01)

(58) Field of Classification Search
 CPC ............. A61B 5/04; A61N 1/00; A61N 1/04; A61N 1/39; A61N 1/3993; A61N 1/37; A61N 1/3925; A61N 1/046; A61N 1/3987; A61N 1/3931; A61N 1/0492; A61N 1/3621; A61N 1/3918; A61N 1/3981; A61N 1/3627; A61N 1/3937; A61N 2001/37294; G01R 31/28
 USPC ......... 324/750.3; 607/4–10, 27, 142
 See application file for complete search history.

(56) References Cited

U.S. PATENT DOCUMENTS

| | | | |
|---|---|---|---|
| 5,645,571 A | 7/1997 | Olson et al. | |
| 5,697,955 A * | 12/1997 | Stolte | 607/5 |
| 6,075,369 A | 6/2000 | Morgan | |
| 6,356,785 B1 * | 3/2002 | Snyder et al. | 607/5 |
| 7,672,720 B2 * | 3/2010 | Heath | 607/5 |
| 2004/0143297 A1 * | 7/2004 | Ramsey, III | 607/5 |
| 2004/0172068 A1 * | 9/2004 | Sullivan et al. | 607/5 |
| 2005/0277991 A1 | 12/2005 | Covey et al. | |
| 2007/0043394 A1 | 2/2007 | Zhang et al. | |
| 2008/0177341 A1 * | 7/2008 | Bowers | 607/5 |
| 2008/0288011 A1 * | 11/2008 | Katzman et al. | 607/5 |
| 2009/0204161 A1 * | 8/2009 | Powers et al. | 607/5 |
| 2010/0114254 A1 * | 5/2010 | Kornet | 607/62 |

* cited by examiner

*Primary Examiner* — Tung X Nguyen
*Assistant Examiner* — Neel Shah
(74) *Attorney, Agent, or Firm* — Novak Druce Connolly Bove + Quigg LLP

(57) ABSTRACT

A defibrillator (1) comprising electrodes (3), a connection (5) for electrically connecting the electrodes together, a defibrillation circuit (9) connected to the electrodes, and an electrode test system (7), comprising
 a test initiation device operable to generate a test initiating signal,
 a test signal generator (15) operable to generate a dc voltage test signal,
 a test signal switch (17) connected to the electrodes and, on receipt of the test initiating signal, operable to connect the electrodes to the test signal generator for passing the dc voltage test signal to the electrodes, and
 a test processing device (19) connected to the test signal switch to receive a dc voltage electrode return signal and process the electrode return signal to determine a pass test result or a fail test result for the electrodes.

19 Claims, 1 Drawing Sheet

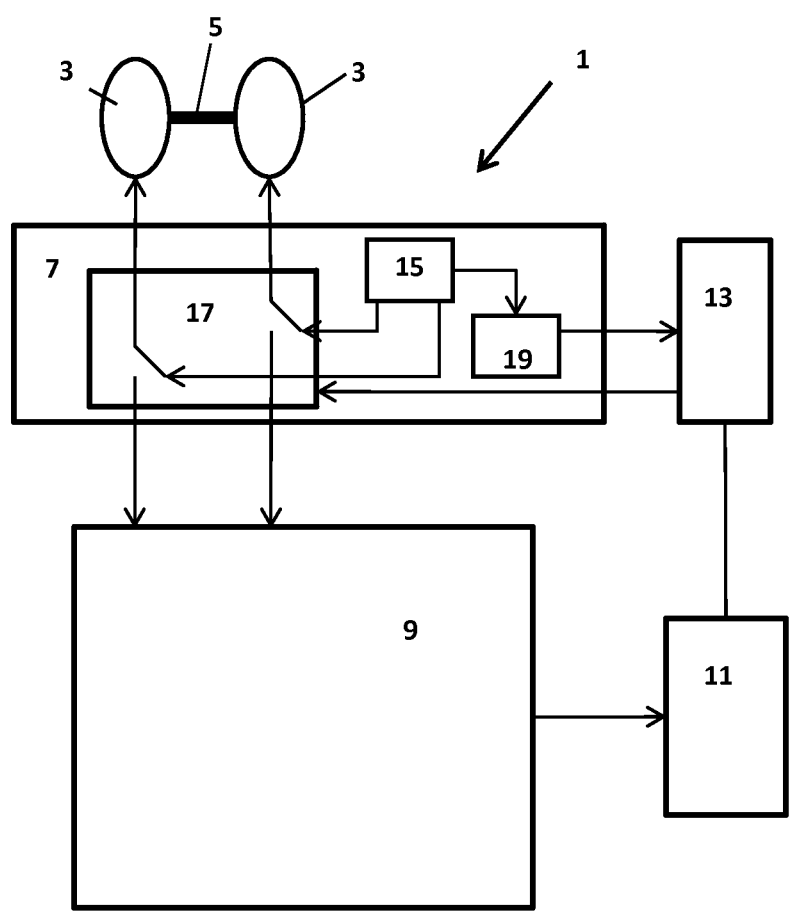

TESTING OF DEFIBRILLATOR ELECTRODES

This invention relates to testing of electrodes for defibrillators, and particularly to the testing of the electrical integrity of the electrodes, i.e. the ability of the electrodes to conduct an electrical signal.

Defibrillators are used to provide a 'shock', i.e. electrical signals, to a patient's heart after occurrence of a cardiac arrest. Studies have shown that the efficacy of a shock decreases significantly as time from the cardiac arrest increases. It is therefore important to use a defibrillator to apply electrical signals to the patient's heart as quickly as possible. This being the case, defibrillators are now frequently found in various public locations, not just in hospitals. In many such locations, a defibrillator may not be used for substantial periods of time. The defibrillator electrodes will usually remain in their packaging during this time. It is important that the electrical integrity of the defibrillator electrodes is maintained over these periods, or, if the integrity is compromised, that this information is made available to a potential user of the defibrillator. This is particularly the case when a defibrillator may be used by a member of the public with little or no experience of defibrillator technology or operation. It is therefore desirable to provide defibrillators with a means by which the integrity of the electrodes may be tested.

According to a first aspect of the invention there is provided a defibrillator comprising electrodes, a connection for electrically connecting the electrodes together, a defibrillation circuit connected to the electrodes, and an electrode test system, comprising a test initiation device operable to generate a test initiating signal, a test signal generator operable to generate a dc voltage test signal, a test signal switch connected to the electrodes and, on receipt of the test initiating signal, operable to connect the electrodes to the test signal generator for passing the dc voltage test signal to the electrodes, and a test processing device connected to the test signal switch to receive a dc voltage electrode return signal and process the electrode return signal to determine a pass test result or a fail test result for the electrodes.

The test initiation device may generate the test initiating signal automatically. The test initiation device may generate the test initiating signal on determination that an electrode test is required, for example as part of an automatic defibrillator self-check process. The test initiation device may generate the test initiating signal on receipt of a manually-derived stimulus.

Electrode tests may be carried out at regular intervals, for example once a week, or once a month, or may be carried out before application of a shock to a patient, or may be carried out on power-up of the defibrillator.

The test signal generator may comprise a dc voltage generator which generates a fixed regulated dc voltage test signal. The dc voltage test signal may have any voltage value compatible with the test signal processor. The dc voltage test signal may have a voltage value of the order of approximately 3V.

The test signal switch may comprise a dual switching device operable simultaneously to pass the dc voltage test signal to the electrodes and to pass the dc voltage electrode return signal to the test processing device. The test signal switch may comprise an electronic switching device such as a transistor. Alternatively or additionally, the test signal switch may comprise an electromagnetic switching device such as an electromagnetic relay. The test signal switch may comprise an analogue multiplexer.

The test processing device may comprise a transistor or a combination of transistors and resistors. The test processing device may be configured such that, on receipt of an electrode return signal, the device either assumes a first state and generates a signal indicating a fail test result, or assumes a second state and generates a signal indicating a pass test result. The test processing device may assume the first state when the electrodes are not electrically conductive and form an open circuit with the test signal generator and the test processing device, and the dc voltage electrode return signal has a voltage value approximately equal to that of the dc voltage test signal. The test processing device may assume the second state when the electrodes are electrically conductive and form a closed circuit with the test signal generator and the test processing device, and the dc voltage electrode return signal has a voltage value of the order of approximately 200 mV.

The test processing device may send the signal indicating a pass test result of the electrodes to a processor of the defibrillator which causes the defibrillator circuit to allow generation of defibrillation signals. The test processing device may send the signal indicating a fail test result of the electrodes to the processor which causes the defibrillator circuit to prevent generation of defibrillation signals. The test processing device may send the signal indicating a fail test result of the electrodes to the processor which causes the defibrillator to issue a warning indicating the fail test result. The warning may be an audible warning. The warning may be a visible warning, such as activation of a warning light provided on the defibrillator.

The test initiation device may comprise a processor. The test processing device may comprise a processor. The test initiation device and the test processing device may comprise a common processor. The test initiation device processor and/or the test processing device processor may be provided by a controller of the defibrillator.

The test initiation device, the test signal generator and the test processing device of the electrode test system may each be implemented in hardware. The test initiation device, the test signal generator and the test processing device may each be implemented on separate integrated circuits or may be implemented together or one or more integrated circuits.

The connection for electrically connecting the electrodes together during a test may be provided by packaging in which the electrodes are stored. The packaging may provide a conductive path from one electrode to the other electrode. The conductive path may be achieved by providing apertures in packaging liners covering gel provided on the electrodes, such that, when placed in the packaging, the electrodes are connected via the exposed gel.

The defibrillator circuit may comprise a patient impedance measurement system connected to the electrodes. The defibrillator may comprise a defibrillator controller connected to the defibrillation circuit.

According to second aspect of the invention there is provided a method of testing electrical conductivity of electrodes of a defibrillator comprising connecting the electrodes together during a test, generating a test initiating signal, generating a dc voltage test signal, operating a test signal switch, on receipt of the test initiating signal, to pass the dc voltage test signal to the electrodes, and receiving a dc voltage electrode return signal from the electrodes and processing the electrode return signal to determine a pass test result or a fail test result for the electrodes.

An embodiment of the invention will now be described by way of example only with reference to the drawing which is a schematic representation of a defibrillator according to the first aspect of the invention.

The drawing shows a defibrillator 1 comprising electrodes 3, a connection 5 for electrically connecting the electrodes together during a test, an electrode test system 7, a defibrillation circuit 9, a patient signal receiver 11 and a defibrillator controller 13. The electrode test system 7 comprises a test signal generator 15, a test signal switch 17 and a test processing device 19. The electrode test system 7 further comprises a test initiation device which, in this embodiment, is provided by the defibrillator controller 13. The components of the defibrillator 1 are connected together as shown in the drawing, for sending and receiving electrical signals between the components.

In use of the defibrillator 1 to apply defibrillation signals to the patient, the electrodes 3 must have electrical integrity, i.e. the ability to conduct an electrical signal. This is determined by testing the electrical conductivity of the electrodes using the electrode test system 7.

The electrodes 3 are resistively connected together, through the connection 5 during the test. In this embodiment, the connection 5 for the electrodes is provided by packaging in which the electrodes are stored and gel placed on each electrode. The packaging provides a conductive path from one electrode to the other electrode. The conductive path is achieved by providing apertures in packaging liners covering the gel provided on the electrodes, such that, when placed in the packaging, the electrodes are connected via the exposed gel. It will be appreciated, however, that other connection means may be used to electrically connect the electrodes together.

The electrode test system 7 operates as follows. The defibrillator controller 13 acting as the test initiation device generates a test initiation signal, on determination by the controller 13 that an electrode test is required as part of an automatic defibrillator self-check process. The test initiation device sends the test initiation signal to the test signal switch 17, which operates to disconnect the electrodes 3 from the defibrillation circuit 9 and connect the electrodes 3 to the test signal generator 15. The test signal generator 15 generates a fixed regulated dc voltage test signal which is applied to the electrodes 3 through a resistor (not shown) and via the test signal switch 17. The resulting dc voltage electrode return signal is applied to the test processing device 19.

The test processing device 19 comprises a transistor (not shown) which is able to assume a first state or a second state according to the electrode return signal received by the test processing device 19. When there is no connection between the electrodes 3, the electrode return signal has a dc voltage value of approximately the fixed regulated voltage signal generated by the test signal generator 15. On receipt of such an electrode return signal, the transistor assumes a first (on) state and generates a fail signal indicating a fail test result. When there is a connection between the electrodes 3, the electrode return signal has a dc voltage value of approximately 200 mV. On receipt of such an electrode return signal, the transistor assumes a second (off) state and generates a pass signal indicating a pass test result.

When the test processing device 19 determines a pass test result of the electrodes 3, it sends the pass signal to the defibrillator controller 13 which causes it to allow generation of defibrillation signals by the defibrillation circuit 9. An electrode pass test result determines that: there is a resistive connection between the electrodes 3; the electrical integrity of the connections to the electrodes 3 is intact; there is a high probability that the electrode construction is within specification. When the test processing device 19 determines a fail test result of the electrodes 3, it sends the fail signal to the defibrillator controller 13 which may cause it to prevent generation of defibrillation signals by the defibrillation circuit 9. The test processing device 19 may also issue a warning signal indicating the fail test result, which may be used to generate a warning such as an audible warning and/or a visible warning e.g. activation of a warning light provided on the defibrillator 1.

The invention claimed is:

1. A defibrillator allowing testing of electrodes, comprising:
   a pair of electrodes;
   a connection for electrically connecting the pair of electrodes together prior to placing the pair of electrodes in contact with a patient;
   a defibrillation circuit connected to the pair of electrodes, wherein the connection directly connects the pair of electrodes separate from the defibrillation circuit; and
   an electrode test system for testing the pair of electrodes prior to the contact, comprising:
   a test initiation device operable to generate a test initiating signal;
   a test signal generator operable to generate a dc voltage test signal;
   a test signal switch connected to the pair of electrodes which, on receipt of the test initiating signal, connects the pair of electrodes to the test signal generator for passing the dc voltage test signal to the pair of electrodes; and
   a test processing device connected to the test signal switch which receives a dc voltage electrode return signal in response to the dc voltage test signal being passed to the pair of electrodes and processes the dc voltage electrode return signal to yield a determination indicating one of a pass test result and a fail test result for the pair of electrodes, wherein the dc voltage electrode return signal substantially equals the dc voltage test signal when the determination indicates the fail test result, and wherein the determination indicates the pass test result when the dc voltage electrode return signal is less than 7% of the dc voltage test signal.

2. The defibrillator of claim 1 in which the test initiation device generates the test initiating signal automatically.

3. The defibrillator of claim 2 in which the test initiation device generates the test initiating signal on determination that an electrode test is required as part of an automatic defibrillator self-check process.

4. The defibrillator of claim 1 in which the test signal generator comprises a dc voltage generator which generates a fixed regulated dc voltage test signal.

5. The defibrillator of claim 1 in which the test signal switch comprises a dual switching device operable to simultaneously pass the dc voltage test signal to the pair of electrodes and to pass the dc voltage electrode return signal to the test processing device.

6. The defibrillator of claim 5 in which the test signal switch comprises an analogue multiplexer.

7. The defibrillator of claim 1 in which the test processing device is configured such that, on receipt of the dc voltage electrode return signal, the test processing device generating a signal indicating one of a fail test result and a pass test result.

8. The defibrillator of claim 7 in which the test processing device generates the pass test result when the pair of electrodes are one of: (1) electrically conductive and form a closed circuit with the test signal generator and the test processing device, and (2) the dc voltage electrode return signal has a voltage value of the order of approximately 200 mV.

9. The defibrillator of claim 7, wherein when the fail test result is indicated by the signal, the test processing device generates an audible warning based on the signal.

10. The defibrillator of claim 7, further comprising:
a warning light, such that when the fail test result is indicated by the signal, the test processing device initiates activation of the warning light.

11. The defibrillator of claim 1 in which the test processing device may send a signal indicating a pass test result of the electrodes to a processor of the defibrillator which causes the defibrillator circuit to allow generation of defibrillation signals.

12. A method of testing electrical conductivity of a pair electrodes of a defibrillator, the method comprising:
connecting the pair of electrodes together, to yield a no-patient contact electrical connection, wherein the no-patient contact electrical connection directly connects the pair of electrodes separate from a defibrillation circuit;
generating a test initiating signal prior to contact with a patient;
generating a dc voltage test signal;
operating a test signal switch, on receipt of the test initiating signal, to pass the dc voltage test signal to the pair of electrodes;
receiving a dc voltage electrode return signal from the pair of electrodes in response to the dc voltage test signal; and
processing the dc voltage electrode return signal to yield a determination indicating one of a pass test result and a fail test result for the pair of electrodes, wherein the dc voltage electrode return signal substantially equals the dc voltage test signal when the determination indicates the fail test result, and wherein the determination indicates the pass test result when the dc voltage electrode return signal is less than 7% of the dc voltage test signal.

13. The method of claim 12, wherein the generating of the test initiating signal, the generating of the dc voltage test signal, the operating of the test signal switch, the receiving of the dc voltage electrode return signal, and the processing of the dc voltage electrode return signal are performed automatically.

14. The method of claim 13, wherein automatic performance is based on an automatic defibrillator self-check process.

15. The method of claim 12, wherein the no-patient contact electrical connection utilizes a gel to conduct electricity between the pair of electrodes.

16. The method of claim 12, further comprising:
when the pass test result is determined, generating a signal indicating the pass test result.

17. The method of claim 12, further comprising:
when the fail test result is determined, generating a signal indicating the fail test result.

18. The method of claim 17, further comprising generating an audible warning based on the signal.

19. The method of claim 17, further comprising activating a warning light based on the signal.

* * * * *